United States Patent

Jung et al.

Patent Number: 5,747,824
Date of Patent: May 5, 1998

[54] APPARATUS AND METHOD FOR SENSING FLUID LEVEL

[75] Inventors: Christopher C. Jung, Mission Viejo; Nader Nazarifar, Laguna Hills, both of Calif.

[73] Assignee: Alcon Laboratories, Inc., Fort Worth, Tex.

[21] Appl. No.: 852,792

[22] Filed: May 7, 1997

Related U.S. Application Data

[63] Continuation of Ser. No. 566,218, Dec. 1, 1995, abandoned.

[51] Int. Cl.$^6$ .................................................... G01F 23/00
[52] U.S. Cl. ........................................... 250/577; 73/293
[58] Field of Search ................................. 250/577, 900; 340/619; 356/436, 442; 73/293

[56] References Cited

U.S. PATENT DOCUMENTS

| | | | |
|---|---|---|---|
| 4,123,227 | 10/1978 | Heim et al. | 23/232 R |
| 4,297,588 | 10/1981 | Hastbacka | 73/293 |
| 4,395,258 | 7/1983 | Wang et al. | 604/65 |
| 4,425,794 | 1/1984 | Duesbury | 73/293 |
| 4,450,722 | 5/1984 | Keyes, IV et al. | 73/293 |
| 4,493,695 | 1/1985 | Cook | 604/27 |
| 4,627,833 | 12/1986 | Cook | 604/34 |
| 4,680,475 | 7/1987 | Transony et al. | 250/577 |
| 4,703,314 | 10/1987 | Spani | 340/619 |
| 4,713,051 | 12/1987 | Steppe et al. | 604/30 |
| 4,758,238 | 7/1988 | Sundblom et al. | 604/319 |
| 4,773,897 | 9/1988 | Scheller et al. | 604/34 |
| 4,790,816 | 12/1988 | Sundblom et al. | 604/31 |
| 4,798,580 | 1/1989 | DeMeo et al. | 604/30 |
| 4,920,336 | 4/1990 | Meijer | 340/619 |
| 5,267,956 | 12/1993 | Beuchat | 604/30 |
| 5,364,342 | 11/1994 | Beuchat et al. | 604/30 |

FOREIGN PATENT DOCUMENTS 1254860  11/1971  United Kingdom.

OTHER PUBLICATIONS

Excerpts from pp. 3-3, 3-13 & 3-14 of the Series Ten Thousand® Ocutome® STTOdx™ Cavitron/Kelman® Phaco-Emulsifier® Aspirator Service Manual; Alcon Laboratories, Inc., 1993.
Schematic, PCB, M/A Pneumatic Control; Dwg. No. 940-8040-025; Alcon Surgical, 1990.
Schematic, PCB, Photocell, Cassette; Dwg. No. 940-8040-002; Cooper Vision, 1987.
Schematic, PCB, LED, Cassette; Dwg. No. 940-8040-001; Cooper Vision, 1987.
Peter Weber: Optical Sensor Measures Filling Levels in Glass Tubes; Feinwerktechnik & Messtechnik, 99, No. 1/2 (1991), pp. 31-33.

*Primary Examiner*—Edward P. Westin
*Assistant Examiner*—Kevin Pyo
*Attorney, Agent, or Firm*—Jeffrey S. Schira

[57] ABSTRACT

An array of four infrared LEDs and an array of four phototransistor receivers with each LED and phototransistor mounted inside a light baffle. The LEDs are positioned in a substantially vertical array just outside one side wall of the cassette. The vertical line on which the LEDs are arranged is substantially parallel to the direction in which the fluid/air interface moves within the cassette. The LEDs are aimed upwardly at an angle of approximately 20° from horizontal. A corresponding substantially vertical array of four phototransistor receivers is mounted outside the cassette opposite the LEDs such that each of the receivers is aimed at its corresponding LED.

22 Claims, 4 Drawing Sheets

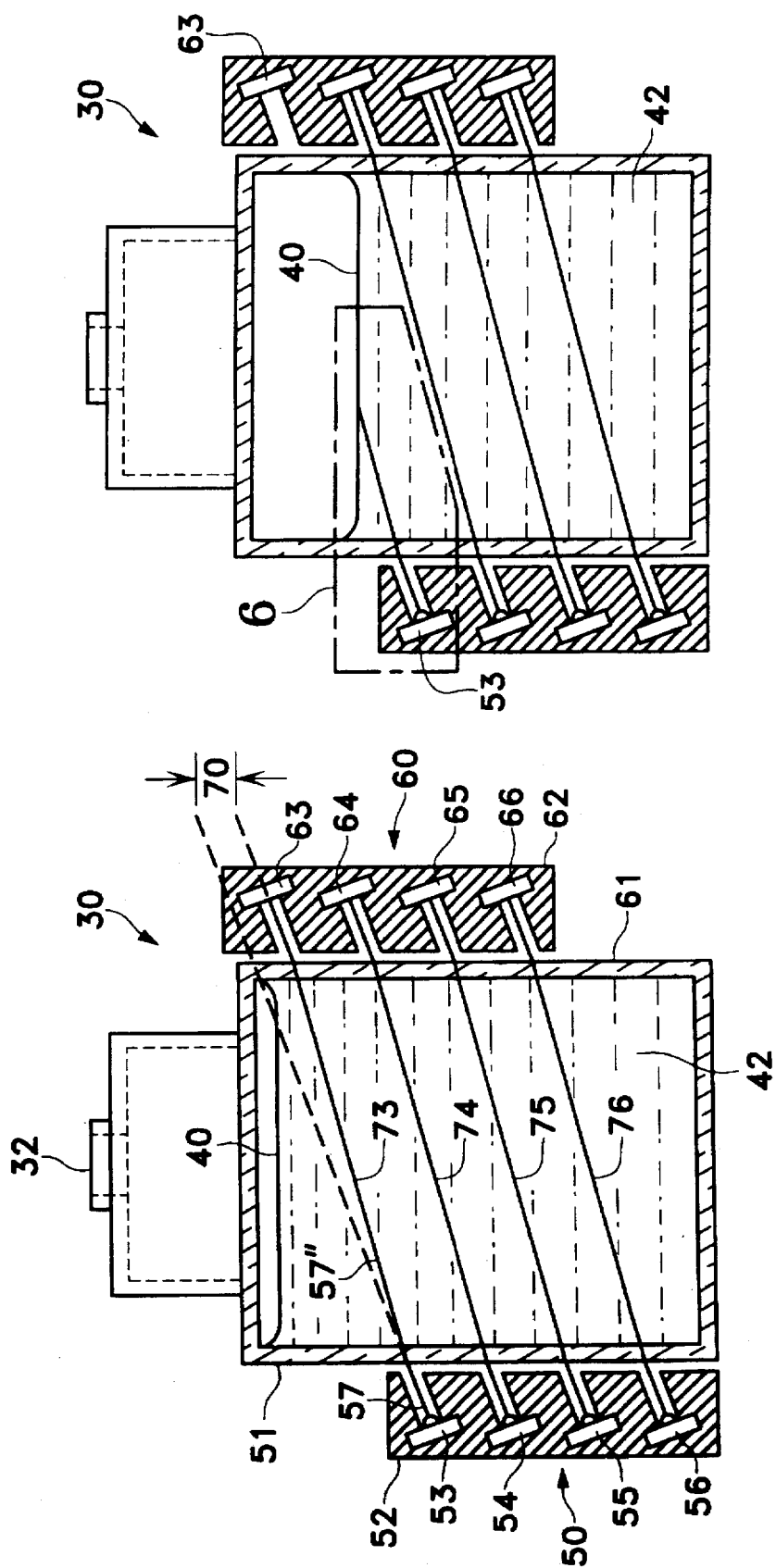

APPARATUS AND METHOD FOR SENSING FLUID LEVEL

This application is a continuation of application Ser. No. 08/566,218, filed Dec. 01, 1995 (now abandoned)).

BACKGROUND OF THE INVENTION

In general, the present invention relates to an apparatus for using the phenomenon of total internal reflection of radiant energy to sense the level of a fluid in a container with walls that are, at least partially, transparent to a given spectrum of radiant energy. More particularly, the present invention relates to an apparatus for sensing the level of fluid within a surgical cassette that is one component of an ophthalmic surgical instrument. Conventional ophthalmic surgical instrument systems use vacuum to aspirate the surgical site and positive pressure to irrigate the site. Typically, a cassette is serially connected between the means used to generate pressure and the surgical instrument. The use of cassettes with surgical instruments to help manage irrigation and aspiration flows at a surgical site is well known. U.S. Pat. Nos. 4,493,695 and 4,627,833 (Cook), 4,395,258 (Wang, et al.), 4,713,051 (Steppe, et al.), 4,798, 850 (DeMeo, et al.), 4,758,238, 4,790,816 (Sundblom, et al.), and 5,267,956 and 5,364,342 (Beuchat) all disclose ophthalmic surgical cassettes with or without tubes, and they are incorporated in their entirety by this reference. Aspiration fluid flow rate, pump speed, vacuum level, irrigation fluid pressure, and irrigation fluid flow rate are some of the parameters that require precise control during ophthalmic surgery.

For aspiration instruments, the air pressure in the cassette is below atmospheric pressure, and fluid within the cassette has been removed from the surgical site. For irrigation instruments, the air pressure in the cassette is higher than atmospheric pressure, and the fluid will be transported to the surgical site. In both types of instruments, the cassette acts as a reservoir for the fluid that buffers variations caused by the pressure generation means.

For the cassette to act as an effective reservoir, the level of fluid (and thus the empty volume) within the cassette must be controlled so that the cassette is neither completely filled nor emptied. If fluid fills the cassette in an aspiration system, fluid may be drawn into the means for generating vacuum (typically a venturi), which would unacceptably interfere with the vacuum level at the surgical instrument. An empty cassette in an aspiration system will result in air being pumped into the drain bag, which would waste valuable reservoir space within the bag. Moreover, constant volume within the cassette in an aspiration system enables more precise control of the level of vacuum within the surgical instrument. Control of the fluid level within cassettes of irrigation systems is similarly desirable.

At least one conventional system, the Series Ten Thousand Ocutome ("STTO") made by Alcon Laboratories, Inc., uses the phenomenon of total internal reflection of radiant energy to sense the fluid level within a surgical cassette. The phenomenon of total internal reflection is a well known physical phenomenon in which radiant energy that contacts an interface between two transmissive substances with different indices of refraction at a sufficiently large angle of incidence (when measured from a line normal to the surface of the interface) is completely reflected by the interface. For an interface between water and air, the angle of incidence at which radiant energy is completely reflected is approximately 48.8° from a line that is normal to the interface. This angle is known as the critical angle.

The STTO employs an array of three infrared light emitting diodes ("LEDs") that are positioned outside one side wall of the cassette in a horizontal line and aimed upward at an angle of about 10° from horizontal (more than 30° less than the 41.2° angle from horizontal that is required for total internal reflection). A corresponding array of three -phototransistor receivers is positioned outside the opposite side wall of the cassette. Each receiver is positioned on the central axis of the beam of infrared energy that is emitted by the corresponding LED. The receiver array is angled downward at approximately 10° from horizontal. Thus, the LED array is aimed at the receiver array and vice versa. The signals received by the receivers are continuously added together and periodically compared to a preset calibration point.

An empty cassette is installed in the surgical console, and during surgery fluid is drawn from the surgical site and into the cassette. The fluid level is allowed to rise until the fluid/air interface blocks the energy from the LED array. When the receiver array stops receiving energy, the system then sounds an alarm indicating that the cassette is full. If the surgical procedure is not finished, the vacuum is turned off and a plug is removed, which allows the cassette to drain.

In operation, the STTO design has difficulty rejecting errors caused by, among other conditions, air bubbles on the wall of the cassette, foam on the surface of the fluid, ambient infrared radiation, and transmission through the meniscus at the wall of the cassette. This problem is caused by the conical shape of the beam emanating from each LED, the horizontal arrangement of the LED and receiver arrays, and the summation, before analysis by the system controller, of the signals received by the phototransistor receivers. The conical beams from the LEDs overlap in the same plane, which allows energy transmitted from one LED to reach more than one phototransistor receiver. Because the energy received by the individual receivers is added together before the control system interprets the received signals, it is not easily possible to detect the presence of a nonfunctioning LED. Additionally, the conical beams from the LEDs result in some of the energy striking the fluid/air interface at an angle significantly greater than the 10° from horizontal at which the central axis of the energy strikes the interface. Some of the energy from the LEDs may even strike the interface at an angle that is greater than the critical angle of a water/air interface of 41.2° from horizontal. Therefore, in such instances, some energy from the LED array may leak through the fluid/air interface even when the central axes of the beams from the LEDs bisect the interface.

SUMMARY OF THE INVENTION

The present invention solves many of the deficiencies associated with systems of the type used on the STTO. One preferred embodiment of the present invention employs an array of four infrared LEDs and an array of four phototransistor receivers with each LED and phototransistor mounted inside a light baffle. The LEDs are positioned in a substantially vertical array just outside one side wall of the cassette. The vertical line on which the LEDs are arranged is substantially parallel to the direction in which the fluid/air interface moves within the cassette. The LEDs are aimed upwardly at an angle of approximately 20° from horizontal. A corresponding substantially vertical array of four phototransistor receivers is mounted outside the cassette opposite the LEDs such that each of the receivers is aimed at its corresponding LED.

Energy from each LED is likely to impinge, if not blocked by the fluid/air interface, only upon its corresponding receiver because the LEDs and receivers are baffled. To further prevent energy from one LED from reaching a receiver other than its corresponding receiver, the LEDs are cycled on and off in sequence such that only one LED is on at a time. Thus, the control system may analyze separately the signal received by each receiver to determine whether energy from each LED has passed through the fluid/air interface. The baffling on the LEDs and receivers also allows the LEDs to be aimed upwardly at about 20° from horizontal rather than the 10° angle from horizontal of the STTO system because stray energy from the LEDs is less likely to encounter the fluid/air interface at an angle greater than 41.2° from horizontal. This 20° nominal angle of transmission gives each LED/receiver pair inherently more margin with which to reject anomalous signals caused by air bubbles within the cassette, foam on the surface of the fluid, and the fluid meniscus among other conditions.

The position of the fluid level over a range of locations and the time-averaged rate of change of the position of the fluid level may be determined because the LED and receiver arrays are positioned in a line substantially parallel to the direction in which the fluid level changes. Based on such information, the controller may more precisely control the volume of fluid within the cassette. Moreover, the system can sense and correct for faults that occur in the LED and receiver arrays. For example, if one of the LEDs stops transmitting, the system can use the information generated by the remaining three LED/receiver pairs to detect that fault and still sense the fluid level in the cassette.

Therefore, one objective of the present invention is to provide an apparatus for optically sensing the fluid level in an ophthalmic surgical cassette over a range of possible locations.

A further objective of the present invention is to provide an apparatus for optically sensing the fluid level in an ophthalmic surgical cassette without instrumentation inside the cassette.

Still another objective of the present invention is to provide an apparatus for optically sensing the fluid level in an ophthalmic surgical cassette that reduces the generation of false sensor readings.

Other objectives, features, and advantages of the present invention will become apparent with reference to the detailed description, drawings and claims that follow.

BRIEF DESCRIPTION OF THE DRAWINGS

FIG. 2 is a cross-sectional view of the fluid level sensing chamber of the cassette shown in FIG. 1 when the chamber is nearly full of fluid and a simplified representation of the radiant sources, transmitted radiant energy, and receivers of one embodiment of the present invention.

FIG. 3 is the cross-sectional view of FIG. 2, but with the fluid/air interface blocking the radiant energy emitted by the uppermost radiant source.

DETAILED DESCRIPTION OF THE DRAWINGS

Figure 1:
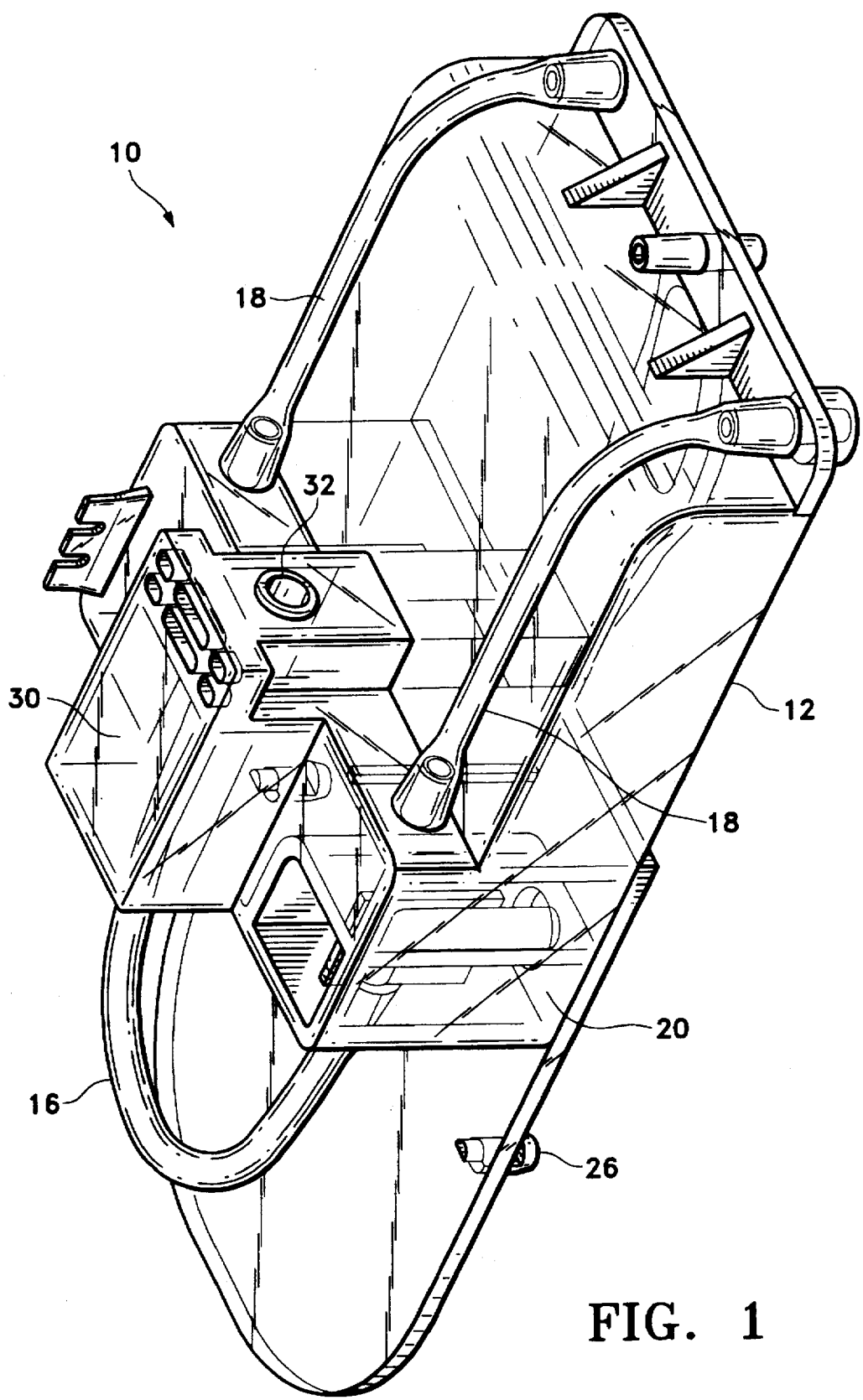
FIG. 1 is a perspective view of a transparent surgical cassette that may be used in conjunction with an embodiment of the present invention.

As best seen in FIG. 1, in one embodiment that may be used with the present invention, cassette 10 generally consists of housing 12, peristaltic pump tube 16, vacuum port 32 and twin aspiration lines 18. Housing 12 preferably is made from transparent plastic and contains chamber 20. When mounted in a surgical console (not shown), cassette is oriented as shown in FIG. 1, with aspiration lines 18 above chamber 20 and pump tube 16 below chamber 20. Negative pressure or vacuum is introduced into chamber 20 through vacuum port 32. Fluid that is aspirated from the surgical site enters chamber 20 through aspiration lines 18. Fluid flows out of chamber 20 through pump tube 16 and is deposited in a drain bag (not shown), which may be attached to housing 12 by use of hooks 26. Fluid level sensing chamber 30 is an extension of chamber 20 such that the fluid level within fluid level sensing chamber 30 corresponds exactly with the fluid level in chamber 20. A vacuum generator (not shown) and a peristaltic pump roller head (not shown) along with appropriate control systems (not shown) may be used to control fluid flows through pump tube 16 and aspiration lines 18 to vary the fluid level within fluid level sensing chamber 30. Cassettes 10 of various types may be installed into the surgical console, depending upon the type of surgical procedure to be performed or the surgeon who will be performing surgery so that the performance of the surgical console is optimized. Each type of cassette 10 must, however, have fluid level sensing chamber 30 of a shape that mates with the fluid level sensing hardware described in the discussion of FIGS. 2–5 immediately below.

FIG. 2 depicts fluid level sensing chamber 30 with port 32. Fluid level sensing chamber 30 is oriented as shown in FIG. 1. LED assembly 50 is mounted within the surgical console (not shown). LED assembly 50 in the embodiment illustrated generally comprises source baffle assembly 52 and LEDs 53–56, each of which emits an infrared beam represented, for example, by central emission axis 57 for LED 53. After passing through cassette wall 51, central emission axis 57 is refracted slightly into central transmission axis 57". In FIG. 2, the infrared beam emitted by each of LEDs 53–56 is transmitted through cassette wall 51, fluid 42, and cassette wall 61 because fluid/air interface 40 is above the beam emitted by LED 53, the uppermost of LEDs 53–56. A more detailed discussion of the behavior of the infrared beams through the cassette wall 51 and in the fluid level sensing chamber 30 is included in connection with FIG. 6. LED assembly 50 is attached to the surgical console such that cassette wall 51 is in close proximity to LEDs 53–56 when cassette 10 is installed in the surgical console. FIGS. 2–5 depict a four-LED embodiment of the present invention but two or three or more than four LEDs (or other suitable radiant sources) may be included in LED assembly 50 without departing from the scope of the invention. FIGS. 2–5 depict source baffle assembly 52 as a single unit for all four LEDs 53–56 but separate source baffles for each of LEDs 53–56 may also be used. Additionally, LEDs 53–56 need not be arranged in a line or on the same side of fluid level sensing chamber 30. LEDs 53–56 may also be offset from each other in directions other than vertical (along with the required offset in the vertical direction), and they may be positioned on different sides of fluid level sensing chamber 30. Of course, receivers 63–66 would need to be similarly repositioned so that they may receive energy from their corresponding LEDs. Such alternate positions for the LEDs and receivers may permit a reduction of the vertical spacing between LED/receiver pairs, which would increase the resolution with which the position of the fluid/air interface 40 could be measured. Positioning the LEDs on different walls of the cassette would enable the system to determine whether the cassette were tilted at an angle from its preferred orientation because the angle of incidence on the fluid/air interface for energy emitted by LEDs on one wall would be different from the angle of incidence for the energy emitted from LEDs on another wall if the cassette were tilted.

Receiver assembly 60 is shown positioned just outside cassette wall 61, which is opposite cassette wall 51. Receivers 63–66 are preferably phototransistors that correspond to LEDs 53–56 respectively. Receivers 63–66 are preferably mounted in receiver baffle assembly 62 and receive the energy emitted by LEDs 53–56 respectively. Receiver baffle assembly 62 may comprise separate baffles as described above in connection with source baffle assembly 52. The positions of receivers 63–66 may be varied in a manner similar to the manner in which the positions of LEDs 53–56 may be varied so long as receivers 63–66 are positioned to receive energy from their corresponding LEDs.

As used herein, the "transmission path" for a particular LED/receiver pair means the path over which the center of the beam of energy emitted by the LED travels until it is received by the receiver. Traces 73, 74, 75, 76 of FIG. 2 substantially correspond to the transmission paths for LED/receiver pairs 53/63, 54/64, 55/65, 56/66 respectively. Traces 73, 74, 75, 76 are not perfectly straight lines because of the refraction that occurs at the interfaces between: (i) the air and cassette wall 51, (ii) cassette wall 51 and fluid 42 or air within fluid level sensing chamber 30, (iii) fluid 42 or air within fluid level sensing chamber 30 and cassette wall 61, and (iv) cassette wall 61 and air. The total effect of the refraction at these interfaces requires that each corresponding receiver 63–66 be positioned slightly lower than otherwise would be required as shown by the offset 70. The total offset 70 is slightly greater when, for example, trace 73 passes through fluid 42 than when trace 73 passes through air within fluid level sensing chamber 30. To accommodate this difference in offsets, receivers 63–66 are preferably positioned about halfway between the theoretically perfect offset positions for transmission through fluid 42 and air.

Figure 5:
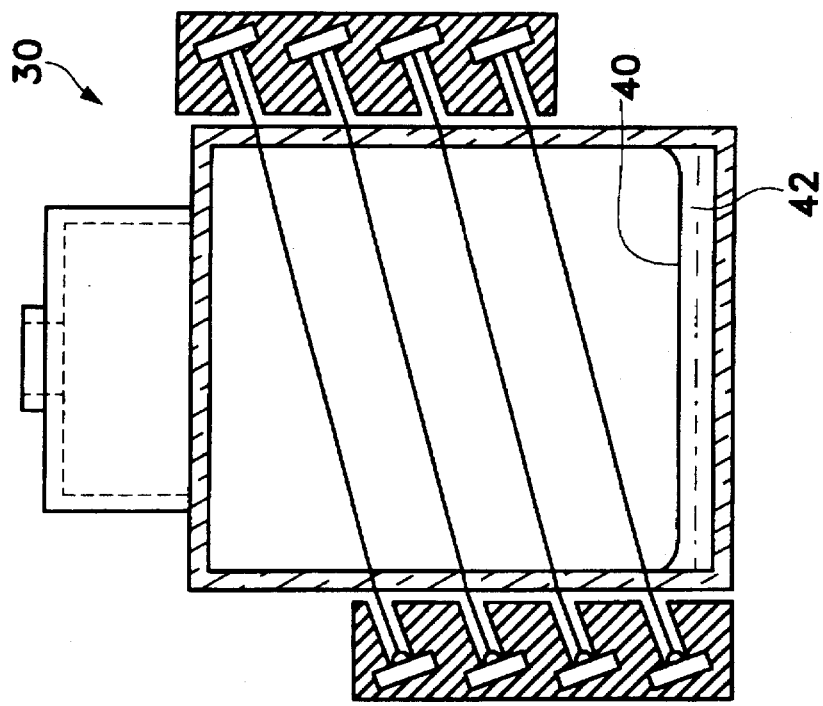
FIG. 5 is the cross-sectional view of FIG. 2, but with the fluid/air interface located below substantially all energy emitted by the radiant sources.
Figure 4:
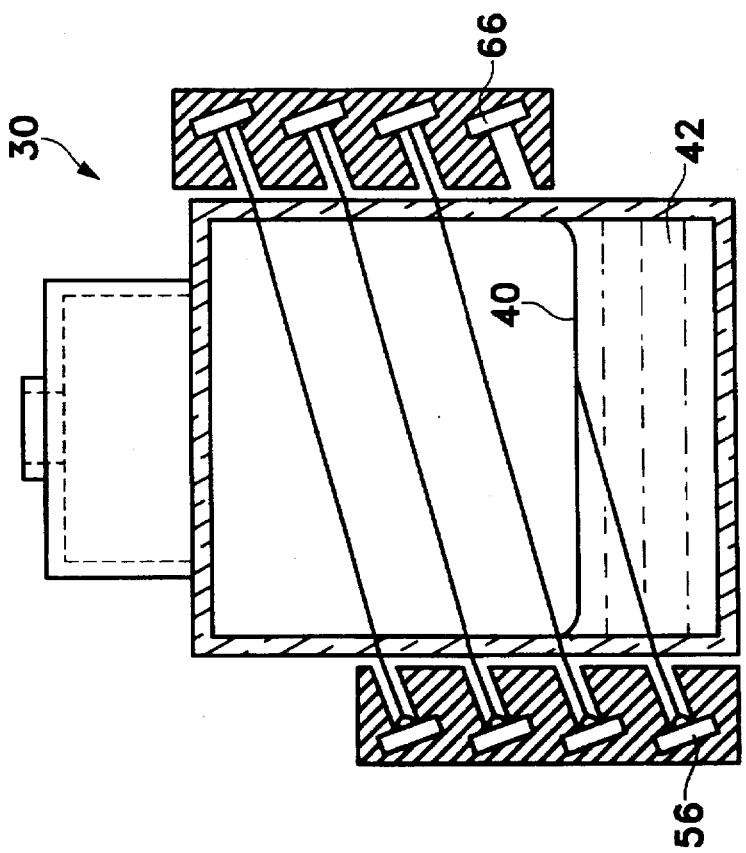
FIG. 4 is the cross-sectional view of FIG. 2, but with the fluid/air interface blocking the radiant energy emitted by the lowermost radiant source.

FIG. 3 depicts fluid/air interface 40 blocking the energy emitted by LED 53 such that receiver 63 receives essentially no signal. FIG. 4 depicts fluid/air interface 40 blocking the energy emitted by LED 56 such that receiver 66 receives no signal. This is the preferred equilibrium position of fluid/air interface 40. FIG. 5 depicts fluid/air interface 40 blocking no energy emitted by LEDs 53–56 such that all receivers 63–66 receive signals. This position of fluid/air interface 40 (or even lower than that shown) is expected when cassette 10 is first installed in the surgical console.

Figure 6:
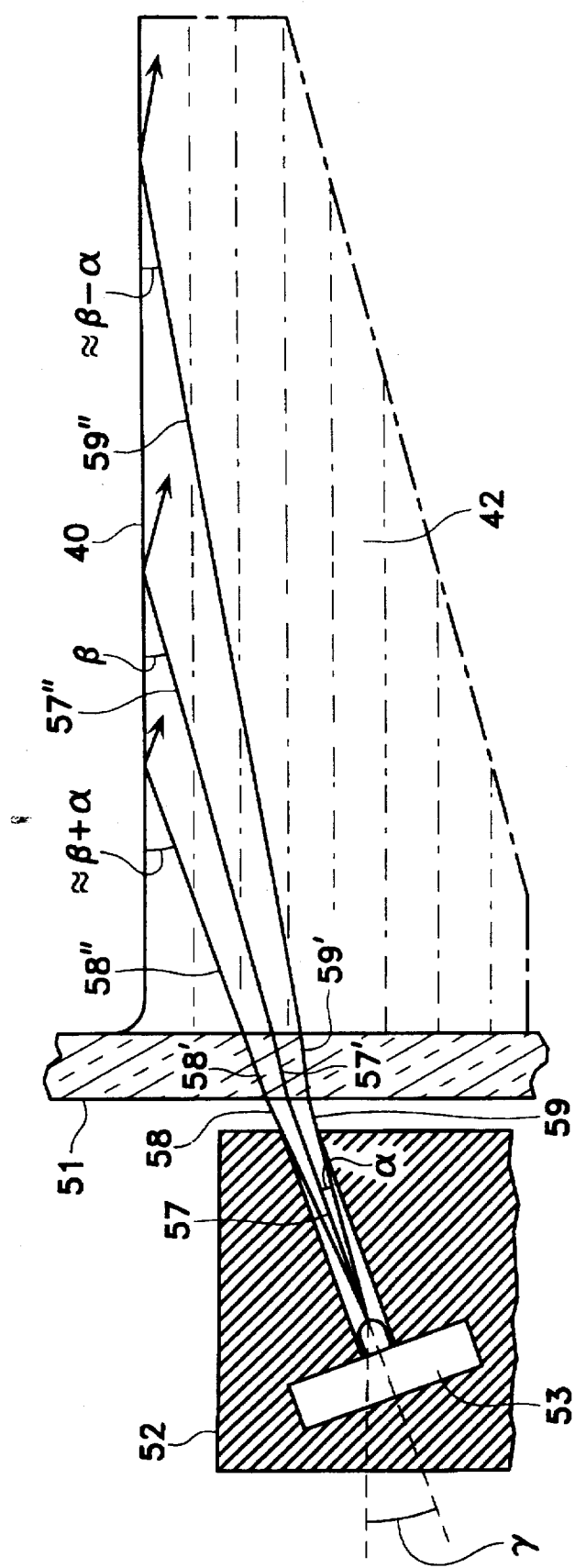
FIG. 6 is a detailed view of the radiant energy emitted by the uppermost radiant source in FIG. 3.

FIG. 6 is a detailed cross-sectional view of fluid level sensing chamber 30 immediately surrounding LED 53 when fluid/air interface 40 is positioned to block energy from LED 53. LED 53 is aimed upward such that central emission axis 57 is at an angle γ of between 0° and 41.2° from horizontal, with about between 5° and 35° from horizontal being preferred, between about 10° and 30° from horizontal being more preferred and about 20° from horizontal being most preferred. Source baffle 52 is narrow enough to block transmission of all energy that is emitted at an angle of more than α of about 5° from central emission axis 57. Thus the beam emitted by LED 53 is defined by upper emission boundary ray 58 and lower emission boundary ray 59, and the angle between rays 58 and 59 is no greater than about 10°. When the beam emitted by LED 53 encounters cassette wall 51, the beam refracts downward about 7° as depicted by upper boundary ray 58', central axis 57', and lower boundary ray 59'. When the beam encounters the other side of cassette wall 51, the beam refracts upward about 2° as depicted by upper transmission boundary ray 58", central transmission axis 57", and lower transmission boundary ray 59". The resulting incidence angle β at which central transmission axis 57" strikes fluid/air interface 40 is about 15°. The incidence angle of upper transmission ray 58" is about 20° (about β+α), and the incidence angle of lower boundary transmission ray 59" is about 10° (about β−α). Because all angles of incidence are less than the 41.2° critical angle (when measured from the horizontal), almost none of the energy from LED 53 penetrates fluid/air interface 40. The meniscus, foam on the surface of fluid 42, splashing of fluid 42, tilting of cassette 10, and air bubbles within fluid 42 or on cassette walls 51 or 61 all create local variations in the angular relationships between the infrared beam and the fluid/air interface 40 described immediately above that may result in a small amount of energy being transmitted through fluid/air interface 40. However, the present invention employs source baffles 52, receiver baffles 62, and certain control techniques described more fully below to reject these and other anomalous signals.

Source baffles 52 and receiver baffles 62 prevent receivers 63–66 from falsely indicating that they have received energy from their corresponding LEDs. Some sources of false readings include reception of energy from the wrong LED (crosstalk) and from ambient infrared sources. Some sources of crosstalk are unpredictable reflection or refraction of energy emitted from LEDs 53–56 caused by, among others, air bubbles in fluid 42 or on cassette walls 51 or 61, the meniscus of fluid 42 where fluid/air interface 40 contacts cassette walls 51 and 61, foam on the fluid/air interface 40, splashing of fluid 42, or extreme tilting of cassette 10. Common sources of ambient infrared include infrared remote control units and incandescent light bulbs. Source baffles 52 and receiver baffles 62 effectively prevent almost all false signals created by ambient infrared and many false signals created by crosstalk.

However, to further prevent errors caused by crosstalk the control system causes LEDs 53, 54, 55, and 56 sequentially to cycle on and off so that only one LED is on at any particular time. The amount of time that each LED is on is determined by the time required for receivers 63–66 to fully turn on in response to receiving energy (approximately one millisecond in a preferred embodiment). The amount of time that all LEDs are off (e.g., the time between turning LED 53 off and turning LED 54 on) is determined by the time required for receivers 63–66 to return to their quiescent (off) state (approximately two milliseconds in a preferred embodiment). Approximately every 100 milliseconds, the control system cycles each of LEDs 53–56 on and off. Immediately before and after each of LEDs 53–56 is turned on, the control system polls each of the corresponding receivers 63–66 respectively to determine whether the receiver was off before the LED came on and then on after the LED came on. This scheme of turning only one LED on at a time and polling the receivers before and after the LEDs are turned on enables the control system to reject false on and false off signals received by any particular receiver.

If the control system determines that a receiver should have been on but was not, then the fluid/air interface 40 must have blocked the signal from the corresponding LED. Thus, the new position of fluid/air interface 40 is known within an acceptable margin. Depending on the new position of the fluid/air interface 40 compared to its previous position, the control system either pumps fluid 42 from chamber 20 or allows more fluid to enter. FIG. 4 depicts the preferred equilibrium position of fluid/air interface 40 such that it interferes with the energy emitted by LED 56 and thus the reception of energy by receiver 66. After achieving the equilibrium position shown in FIG. 4, the control system turns the peristaltic pump off and allows fluid to collect in chamber 20. By contrast, if the control system detects fluid/air interface 40 with any of LED/receiver pairs 53/63, 54/64, or 55/65, or if the fluid/air interface 40 rises to allow passage of trace 76 to receiver 66, then the control system turns the peristaltic pump on and drains fluid 42 from chamber 20 until the equilibrium position is attained again.

When a cassette is first installed in the surgical console, the control system automatically tries to pump fluid from chamber 20. If, after about 10 seconds, a fluid/air interface is not detected, chamber 20 is assumed to be empty and fluid is allowed to accumulate until the equilibrium position shown in FIG. 4 is reached. If, during this initial pump down period, fluid/air interface is detected by LED/receiver pair 53/63, then chamber 20 is assumed to have been full and is pumped down to the equilibrium position. Once equilibrium is achieved, the control system operates as described immediately above.

In an alternate embodiment of the present invention, receivers 63–66 may be positioned such that they receive energy only when the energy is reflected downward by fluid/air interface 40. In such an alternate embodiment, LEDs 53–56 would be positioned as shown in FIGS. 2–5, but receivers 63–66 would be moved lower and angled with their open ends facing upward at an angle of about 20°. Thus, the interface would be detected by the presence of a received signal rather than the absence of a signal.

The foregoing is provided for the purposes of description rather than limitation. Changes, modifications, or adaptations may be made to the apparatus for sensing the fluid level within a surgical cassette and components described in the foregoing and the remainder of this document without departing from the scope or spirit of the invention.

We claim:

1. An apparatus for detecting a fluid level contained within a transparent fluid reservoir having an outer surface, the apparatus comprising:
   a) a plurality of radiant sources positioned vertically outside of the outer surface of the reservoir so that the radiant sources do not contact the fluid, each of the radiant sources emitting a beam of energy into the reservoir substantially along a transmission path that is angled so that the beam of energy does not penetrate an air/fluid interface; and
   b) a plurality of receivers positioned vertically outside of the outer surface of the reservoir so that the receivers do not contact the fluid, each receiver being aligned along the transmission path of one of the plurality of radiation sources.

2. The apparatus of claim 1 further comprising:
   a) a source baffle attached to each radiant source; and
   b) a receiver baffle attached to each receiver.

3. The apparatus of claim 1 wherein there are at least three radiant sources and at least three receivers.

4. The apparatus of claim 1 wherein the radiant sources are light emitting diodes and the receivers are phototransistors.

5. The apparatus of claim 4 further comprising:
   a) a source baffle attached to each light emitting diode; and
   b) a receiver baffle attached to each phototransistor.

6. The apparatus of claim 5 wherein the light emitting diodes are turned on and turned off sequentially such that only one light emitting diode is on at any given time.

7. The apparatus of claim 2 wherein there are at least three radiant sources and at least three receivers.

8. The apparatus of claim 6 wherein:
   a) the source baffle blocks energy that is emitted by its corresponding light emitting diode at an angle of greater than about five degrees from the corresponding transmission path, and
   b) the receiver baffle prevents the phototransistors to which the receiver baffle is attached from receiving energy from an angle of more than about five degrees from the corresponding transmission path.

9. The apparatus of claim 8 wherein the light emitting diodes emit infrared radiation.

10. The apparatus of claim 4 wherein the light emitting diodes emit infrared radiation.

11. The apparatus of claim 5 wherein there are at least three light emitting diodes and at least three phototransistors.

12. The apparatus of claim 1 wherein the radiant sources are turned on and turned off sequentially such that only one radiant source is on at a time.

13. The apparatus of claim 4 wherein the light emitting diodes are turned on and off sequentially such that only one LED is on at a time.

14. An apparatus for detecting a level of a fluid within a surgical cassette, the surgical cassette having a first cassette wall and a second cassette wall, the fluid being contained between the first cassette wall and the second cassette wall, comprising:
   a) a first light emitting diode positioned outside of the first cassette wall so that the first light emitting diode does not contact the fluid, and so that the first light emitting diode emits radiation predominantly along a first transmission path, the first transmission path being aimed upwardly at an angle so that the radiation does not penetrate a air/fluid interface when the air/fluid interface intersects the first transmission path; and
   b) a first source baffle mounted on the first light emitting diode so that the first source baffle blocks any energy emitted by the first light emitting diode at an angle of greater than about five degrees from the first transmission path;
   c) a first phototransistor positioned outside of the second cassette wall so that the first phototransistor does not contact the fluid, and so that the first phototransistor receives radiation along the first transmission path from the first light emitting diode;
   d) a first receiver baffle mounted on the first phototransistor such that the first receiver baffle prevents energy from impinging upon the first phototransistor from a direction of greater than about five degrees from the first transmission path;
   e) a second light emitting diode positioned outside of the first cassette wall so that the second light emitting diode does not contact the fluid and so that the second light emitting diode emits radiation predominantly along a second transmission path, the second transmission path being aimed upwardly at an angle so that the radiation does not penetrate the air/fluid interface when the air/fluid interface intersects the second transmission path;
   f) a second source baffle mounted on the second light emitting diode so that the second source baffle blocks any energy emitted by the second light emitting diode at an angle of greater than about five degrees from the second transmission path;

g) a second phototransistor positioned outside of the second cassette wall so that the second phototransistor does not contact the fluid, and so that the second phototransistor receives radiation along the second transmission path from the second light emitting diode;

h) a second receiver baffle mounted on the second phototransistor such that the second receiver baffle prevents energy from impinging upon the second phototransistor from a direction of greater than about five degrees from the second transmission path;

i) a third light emitting diode positioned outside of the first cassette wall so that the third light emitting diode does not contact the fluid, and so that the third light emitting diode emits radiation predominantly along a third transmission path, the third transmission path being aimed upwardly at an angle so that the radiation does not penetrate the air/fluid interface when the air/fluid interface intersects the third transmission path;

j) a third source baffle mounted on the third light emitting diode so that the third source baffle blocks any energy emitted by the third light emitting diode at an angle of greater than about five degrees from the third transmission path;

k) a third phototransistor positioned outside of the second cassette wall so that the third phototransistor does not contact the fluid, and so that the third phototransistor receives radiation along the third transmission path from the third light emitting diode;

l) a third receiver baffle mounted on the third phototransistor such that the third receiver baffle prevents energy from impinging upon the third phototransistor from a direction of greater than about five degrees from the third transmission path;

m) a fourth light emitting diode positioned outside of the first cassette wall so that the fourth light emitting diode does not contact the fluid, and so that the fourth light emitting diode emits radiation predominantly along a fourth transmission path, the fourth transmission path being aimed upwardly at an angle so that the radiation does not penetrate the air/fluid interface when the air/fluid interface intersects the fourth transmission path;

n) a fourth source baffle mounted on the fourth light emitting diode so that the fourth source baffle blocks any energy emitted by the fourth light emitting diode at an angle of greater than about five degrees from the fourth transmission path;

o) a fourth phototransistor positioned outside of the second cassette wall so that the fourth phototransistor does not contact the fluid, and so that the fourth phototransistor receives radiation along the fourth transmission path from the fourth light emitting diode; and p) a fourth receiver baffle mounted on the fourth phototransistor such that the fourth receiver baffle prevents energy from impinging upon the fourth phototransistor from a direction of greater than about five degrees from the fourth transmission path.

15. An method of detecting a fluid level contained within a transparent fluid reservoir having an outer surface, the method comprising the steps of:

a) causing a plurality of radiant sources positioned vertically outside of the outer surface of the reservoir so that the radiant sources do not contact the fluid sequentially to emit a beam of energy into the reservoir substantially along a transmission path that is angled so that the beam of energy does not penetrate an air/fluid interface; and b) detecting the energy beams emitted by the plurality of radiation sources using a plurality of receivers positioned vertically outside of the outer surface of the reservoir so that the receivers do not contact the fluid, each receiver being aligned along the transmission path of one of the plurality of radiation sources.

16. The method of claim 15 wherein:

a) a source baffle is attached to each radiant source; and b) a receiver baffle is attached to each receiver.

17. The method of claim 15 wherein there are at least three radiant sources and at least three receivers.

18. The method of claim 15 wherein the radiant sources are light emitting diodes and the receivers are phototransistors.

19. The method of claim 18 wherein:

a) a source baffle is attached to each light emitting diode; and b) a receiver baffle is attached to each phototransistor.

20. The method of claim 16 wherein there are at least three radiant sources and at least three receivers.

21. The method of claim 20 wherein:

a) the source baffle blocks energy at an angle of greater than about five degrees from the corresponding transmission path from being emitted by the light emitting diode to which the source baffle is attached, and b) the receiver baffle prevents the phototransistors to which the receiver baffle is attached from receiving energy from an angle of more than about five degrees from the corresponding transmission path.

22. The method of claim 21 wherein the light emitting diodes emit infrared radiation.

* * * * *